United States Patent [19]

Posen et al.

[11] Patent Number: 5,732,396
[45] Date of Patent: Mar. 24, 1998

[54] HEARING AID SCREENING DEVICE HAVING AN ELONGATED SPACING ELEMENT WHICH EXTENDS THEREFROM PROVIDING FOR INGRESS OF BACKGROUND NOISE

[75] Inventors: Lawrence M. Posen, Glencoe; Miles P. Posen, Chicago; Erik A. Lindberg, Sleepy Hollow, all of Ill.

[73] Assignee: Beltone Electronics Corporation, Chicago, Ill.

[21] Appl. No.: 731,119

[22] Filed: Oct. 9, 1996

Related U.S. Application Data

[63] Continuation of Ser. No. 191,798, Feb. 3, 1994, abandoned.
[51] Int. Cl.$^6$ ................... G10L 3/00; A61B 1/22
[52] U.S. Cl. ................... 704/267; 73/585; 704/271
[58] Field of Search ................... 73/585; 395/2.67, 395/2.69, 2.7, 2.76, 2.79, 2.8

[56] References Cited

U.S. PATENT DOCUMENTS

| | | |
|---|---|---|
| D. 324,913 | 3/1992 | Chojar . |
| D. 335,349 | 5/1993 | Lyon et al. ............... D24/151 |
| 5,081,441 | 1/1992 | Chojar . |
| 5,197,332 | 3/1993 | Shennib ............... 73/585 |
| 5,291,785 | 3/1994 | Downs ............... 73/585 |

OTHER PUBLICATIONS

L.S. Alvord et al., *Reference Equivalent Threshold Levels For The Handtronix, Oto–Screener,* Journal of the Acoustical Society of America, 91(4), Pt. 1, Apr. 1992.

"Miniature audiometric devices: Are they clinically accurate", Lynn S. Alvord, Ph.D., believed to have been published in 1933; and.

Advertisement for Oto–Screen I, by Handtronix of Salt Lake City, Utah, believed to have been published in 1990.

"Hear Pen," Roy F. Sullivan, PhD., wich is a reprint from Hearing Instruments, vol. 43, No. 4, 1992.

*Primary Examiner*—Allen R. MacDonald
*Assistant Examiner*—Patrick N. Edouard
*Attorney, Agent, or Firm*—Dressler, Rockey, Milnamow & Katz, Ltd.

[57] ABSTRACT

A hand held hearing screening device includes a housing with a spacing element extending therefrom. Word generating circuitry is carried within the housing. A control switch on the housing cycles the generating circuitry to produce one or more output word or phrase sequences.

12 Claims, 4 Drawing Sheets

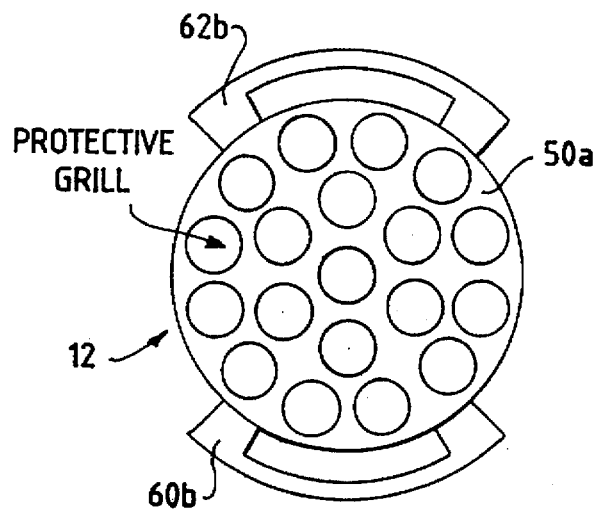
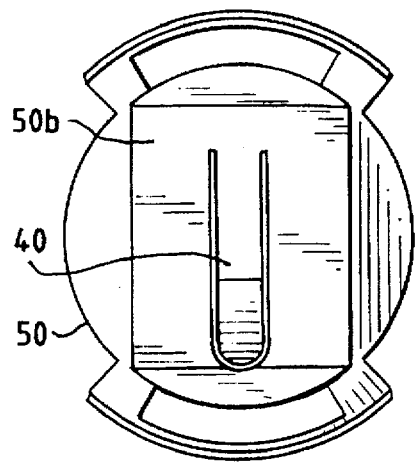
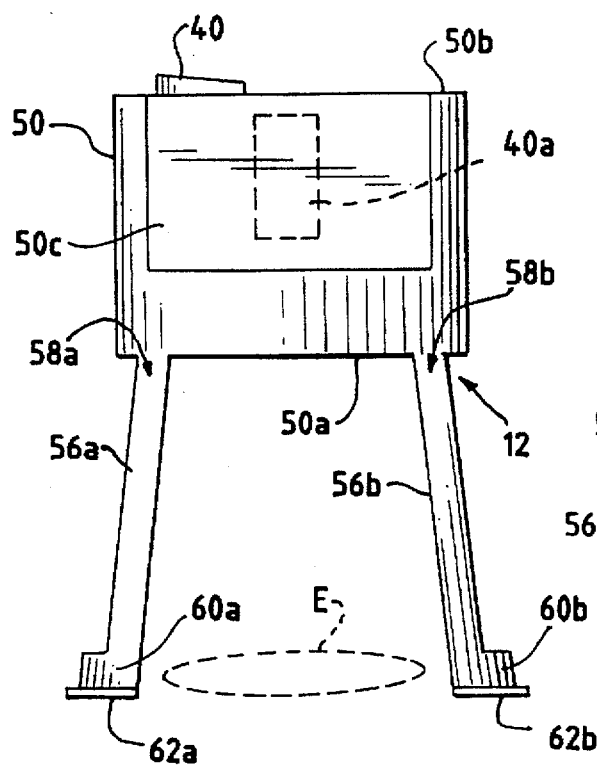
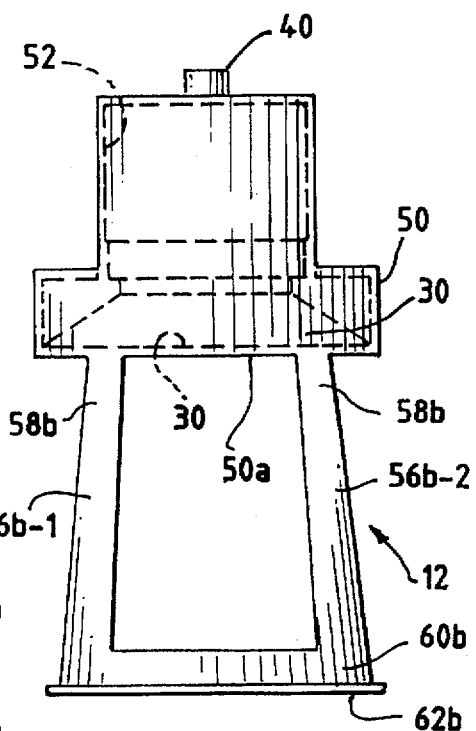

HEARING AID SCREENING DEVICE HAVING AN ELONGATED SPACING ELEMENT WHICH EXTENDS THEREFROM PROVIDING FOR INGRESS OF BACKGROUND NOISE

This is a continuation of application Ser. No. 08/191,798, filed Feb. 3, 1994 now abandoned.

FIELD OF THE INVENTION

The invention pertains to portable screening devices. More particularly, the invention pertains to portable, relatively low cost, devices for generating words or phrases for hearing screening purposes.

BACKGROUND OF THE INVENTION

The advent of the integrated circuit and the evolution of related manufacturing techniques has made it possible to reduce the overall size, weight and energy requirements for hearing aids dramatically over the last twenty years. Current hearing aid products can be inserted into a user's ear canal and can provide substantial improvements in an individual's ability to participate in and enjoy conversations or other audible frequency stimuli.

Notwithstanding the advances that have been made in the reduction in size and improved performance of hearing aids, there continues to he an ongoing threshold issue of making the general population aware of potential hearing problems. It is possible to evaluate an individual's hearing using an audiometer or other hearing evaluation device. However, the equipment for doing so is usually expensive and complex and requires a substantial level of skill to carry out an evaluation.

In an attempt to provide less expensive and easier to use screening devices, as opposed to hearing evaluation devices, there has been an interest in inexpensive portable screening devices which generate one or two audible tones. The selected tone or tones are presented at a frequency or frequencies and with a sufficient energy level that an individual with normal hearing levels can be expected to readily hear the tone or tones. An inability to hear the tone or tones indicates that a further evaluation may be necessary.

The known devices while portable, relatively inexpensive and easy to operate, are very limited in the type of output that is produced. The hearing process is a complex phenomenon which goes far beyond the basic ability to hear one or more tones. Individuals do not normally communicate using tones. Instead, audibly discernible words and phrases are usually used.

Further, it has been observed that persons having the same audiogram configuration often perform differently in understanding speech. This is because hearing impairment is also a complex phenomenon involving more than a simple loss of sensitivity for quiet sounds, which is what the audiogram reports.

Hearing impairment can also include recruitment (less loss for higher level signals than lower level signals), loss of frequency resolution, and loss of temporal resolution. All of these factors combine to affect how a person with a hearing impairment functions in his/her acoustic environment. The most important hearing tasks for a person is understanding other people talking.

Thus, there continues to be a need for relatively inexpensive, easy to use audible screening devices which provide more realistic audible outputs than a simple preselected tone or tones. Preferably, such devices could be readily used by the general population without extensive education for the purpose of enabling an individual from time to time to determine whether or not his or her ability to hear words and phrases at normal energy levels has been impaired.

SUMMARY OF THE INVENTION

An apparatus which produces words or phrases in accordance with the present invention includes a housing with a positioning member which extends therefrom. Vocabulary circuitry, carried within the housing, digitally stores a preselected plurality of words or phrases to be reproduced.

In one aspect, the words or phrases are organized as a single list. In another aspect, two or more lists can be created.

Where there is a single list, those words or phrases can be presented to both ears of an individual. Where there are two or more lists, different lists can be presented to each ear.

A manually operable switch is carried by the housing for initiating an audible output. Processing circuitry, carried by the housing is responsive to the switch.

The processing circuitry extracts at least one member of the operative plurality of words or phrases from the storage circuitry. A determination is also made as to one or more members to be extracted subsequently.

Output circuitry, carried by the housing is responsive to the processing circuitry. Various representations of the extracted members can be produced. In one aspect, the output circuitry includes an output transducer for producing an audible output. Alternately, electromagnetic, ultrasonic, infrared or vibratory outputs can be produced.

In another aspect, the processing circuitry can include a programmed logic array. Alternately, a programmed processor or wired logic could be used. Tone storage circuitry as well as noise generation circuitry can be coupled to the vocabulary circuitry. The apparatus can further include output control circuitry coupled to the processing circuitry.

In yet another aspect, the positioning member of the housing can extend therefrom a predetermined distance. The distal end of the member defines a contact surface.

The contact surface can be located adjacent to an ear of a person for screening purposes. The positioning member locates the output transducer a predetermined distance from the individual's ear.

These and other aspects and attributes of the present invention will be discussed with reference to the following drawings and accompanying specification.

BRIEF DESCRIPTION OF THE DRAWING

FIGS. 4A through 4D are a plurality of views of the housing and component locations of a screening apparatus.

DETAILED DESCRIPTION OF THE PREFERRED EMBODIMENT

Figure 1:
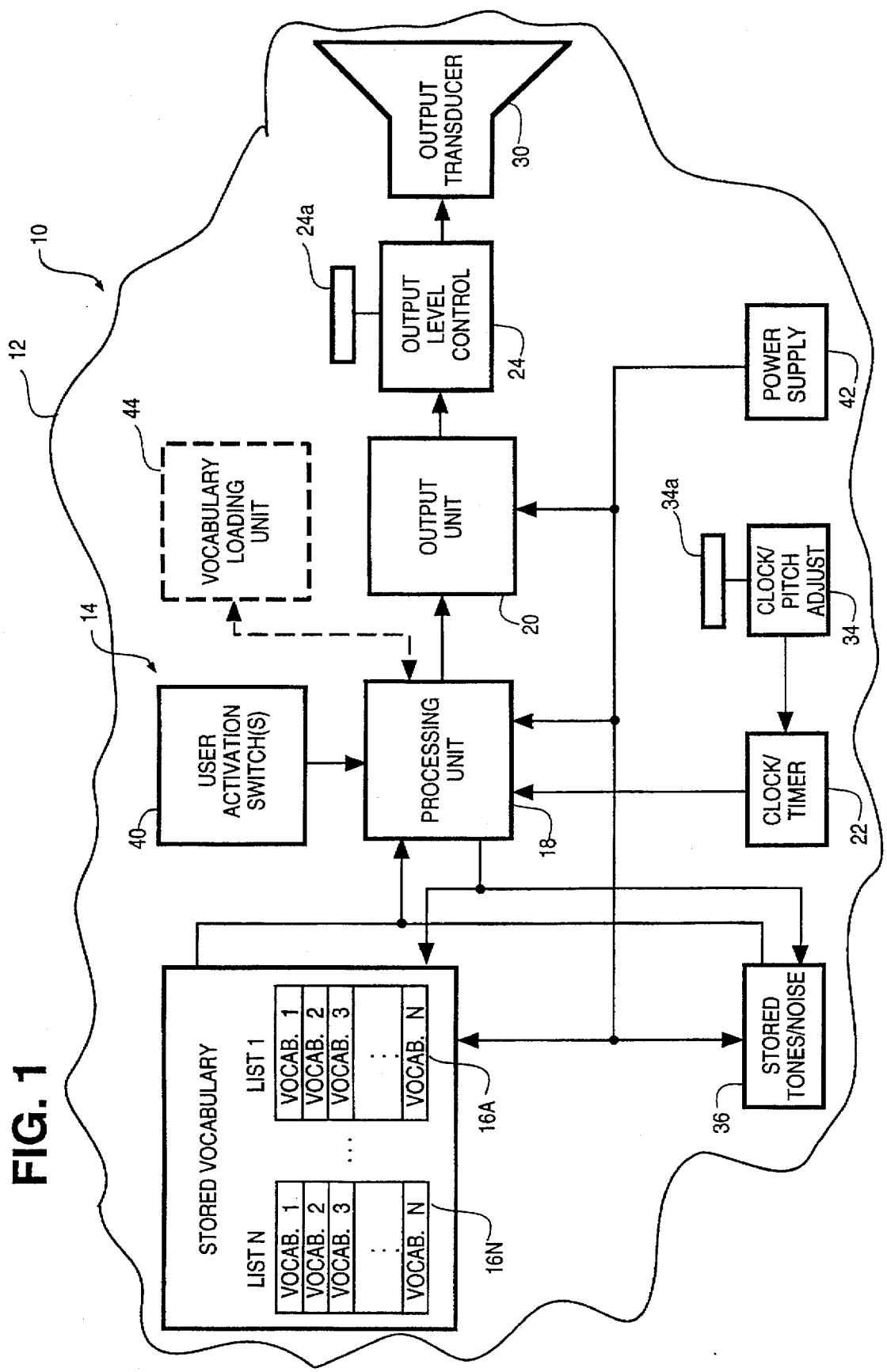
FIG. 1 is a block diagram illustrating electronic components of a screening apparatus.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

FIG. 1 is a block diagram of an apparatus 10 usable for audible screening purposes. The apparatus 10 includes a housing generally indicated at 12.

The housing 12 carries a plurality of electronic components 14 including one or more vocabulary lists indicated at 16A through 16N. Other output stimuli could be provided. The lists 16A through 16N are organized to store a plurality of predetermined words or phrases usable for screening purposes.

The vocabulary words or phrases can be stored in either a digital or an analog fashion. It will be understood that the details as to how the storage is implemented are not a limitation of the present invention. For example, the predetermined words or phrases could be stored digitally in either ROM or RAM memory. Alternately, if desired, analog storage could be used.

It will further be understood that the number of vocabulary words or phrases in any individual list, such as the representative indicated list 16A, can vary without departing from the spirit and scope of the present invention. What is required is that there be a sufficient number of words or phrases stored such that a user of the apparatus 10 will have an opportunity to try a large enough sample of words or phrases to experience a meaningful screening activity.

Coupled to the one or more lists 16A through 16N is a processing unit 18 which can be implemented as a programmable logic array. Alternately, the processing unit 18 can be implemented as a programmed processor or with hard wired logic.

Coupled to the processing unit 18 is an output unit 20. The unit 20 receives an input from the processing unit 18 and, one or more of the lists 16A through 16N. In addition, the processing unit 18 receives an input from a clock/timer element 22.

Output from the unit 20 is coupled to an output level control unit 24 which in turn drives an output transducer 30.

The output transducer 30 could be implemented, for example, as a speaker to provide audible output, or as a bone conductor to provide stimulus to the ear through vibration. Alternately, instead of a transducer which generates sound waves, a transducer which utilizes ultrasonic, infrared or electromagnetic induction to couple to another transducer being worn by the individual being screened, can be used without departing from the spirit and scope of the present invention.

The output level control unit 24 may include a manually operable adjustment 24a. This results in having a wide range of output levels available which makes the apparatus 10 effective for different purposes.

Where an individual being screened is unable to discern the audible words or phrases from the output transducer 30, the output level can be increased using the control element 24a. The degree of increase necessary will give an indication of the severity of a particular hearing loss.

Input to the clock/timer element 22 is provided by a clock/pitch adjusting element 34 having an adjustment input 34a. As a result of being able to adjust the element 34, the fundamental pitch of the audible output being produced can be increased or decreased.

In addition to prestored vocabulary lists, such as lists 16A through 16N, prestored tones and noise are provided in an element 36. It is useful to integrate tones and/or noise with the words or phrases being presented to a user.

Tones, for example, could be used as signals to indicate that a word or a phrase is about to be presented. Additionally, noise signals or tones could be used for calibrating the unit or in combination with words or phrases to address specific types of hearing deficiencies.

One or more user activatable switches or control elements 40 are carried by the housing 12 and are in turn, electrically coupled to the processing unit 18. The user is able to manipulate one or more manually operable switches or control elements to indicate to the processing unit 18 that the next word or phrase is to be presented or the apparatus 10 is to be initialized or that the unit 18 should start accessing a different prestored vocabulary list.

The apparatus 10 is energized by a power supply 42 which could be a battery. Additionally, the unit 10 could be equipped with an AC adapter, an external power supply or other sources of electrical energy.

Rather than having a prestored fixed group of vocabulary lists, the lists 16A through 16N could be alterable and could be loadable through a plug-in vocabulary loading unit 44 (illustrated in phantom in FIG. 1). The vocabulary loading unit 44 could incorporate, for example, a programmable computer or the like for ease of creating and/or modifying vocabulary lists.

It will be understood that the words or phrases stored in the lists 16A through 16N could be in a variety of languages and could also focus on one particular type of hearing loss, such as the loss exhibited in the presence of monosyllabic high frequency emphases words, by way of example.

Figure 2:
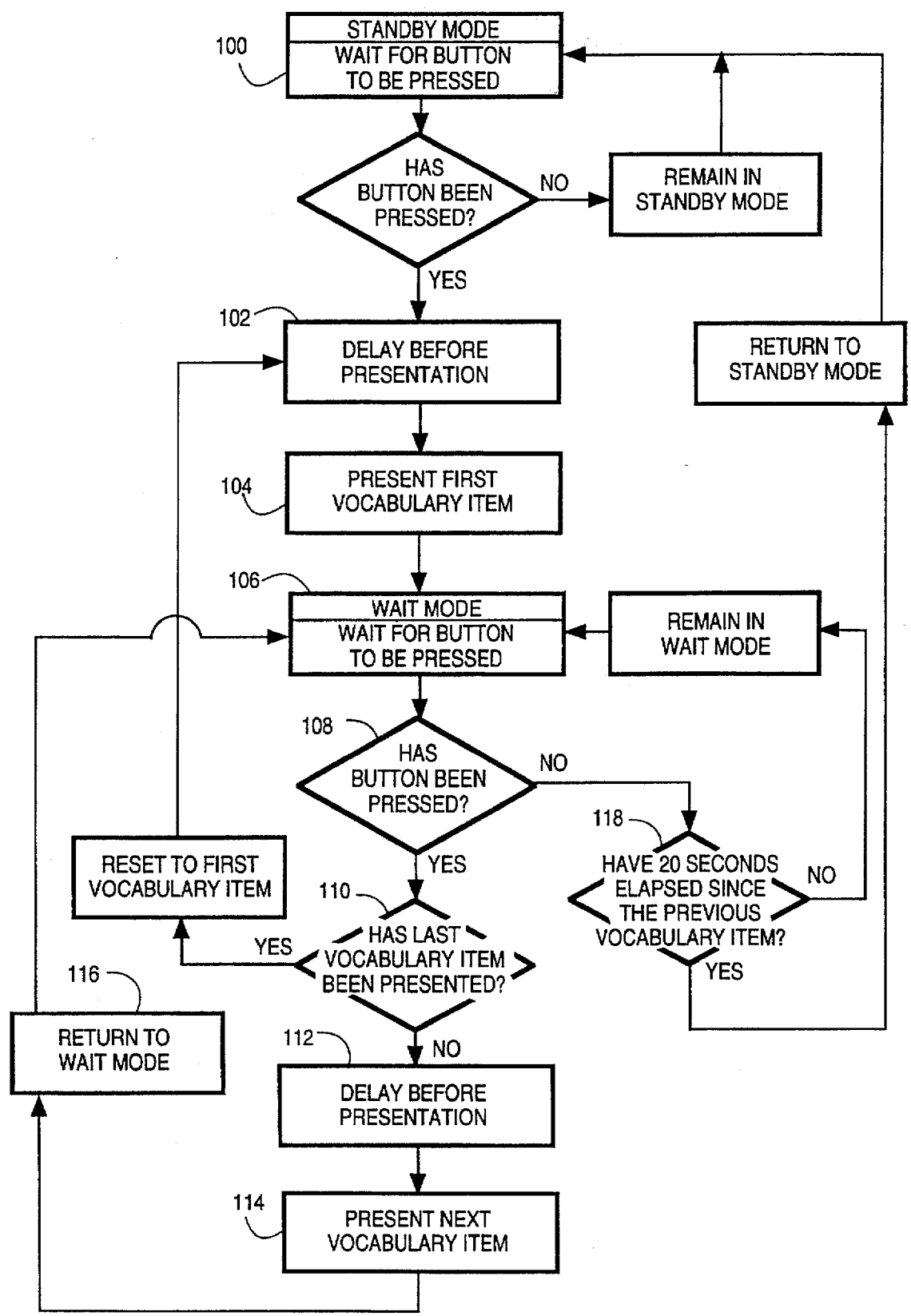
FIG. 2 is a flow diagram illustrating a particular embodiment of a screening method.

FIG. 2 illustrates an embodiment of a method in accordance with the present invention which illustrates one way in which the unit 10 can function. In a step 100, the unit 10 is in a standby mode waiting for a command button to be pressed. Once a command button has been pressed, a delay is provided in a step 102.

In a step 104, the next vocabulary word or phrase from the active list is accessed, such as from the list 16A for example, and processed by both the processing unit 18 and the output unit 20 to provide an output via the transducer 30. It will be understood that other forms of output stimuli could be presented.

Subsequent to the step 104, the unit 10 reenters the wait mode in a step mode 106 and awaits for another input command via the user activation elements 40. In response to one of the command elements having been activated, within a predetermined period of time, in a step 108, a determination is made as to whether or not the last word or phrase in the active list has been presented in a step 110. If not, after a delay in a step 112, the next element in the list is then presented via the transducer 30 in a step 114. The unit 10 then returns to the wait mode in the step 116.

In the event that a control element has not been activated within a predetermined period of time, illustrated in a step 118, corresponding to 20 seconds for example, the unit automatically returns to the standby mode and the step 100.

It will be understood that the method illustrated in FIG. 2 is one of a variety of ways in which the apparatus 10 can operate. For example, the time delay illustrated in step 118, can be eliminated if desired. Alternately, one or more of the activation elements 40 can be used to specify one or more of the prestored lists 16A through 16N or to indicate whether or not a right ear or a left ear is being screened.

Figure 3:
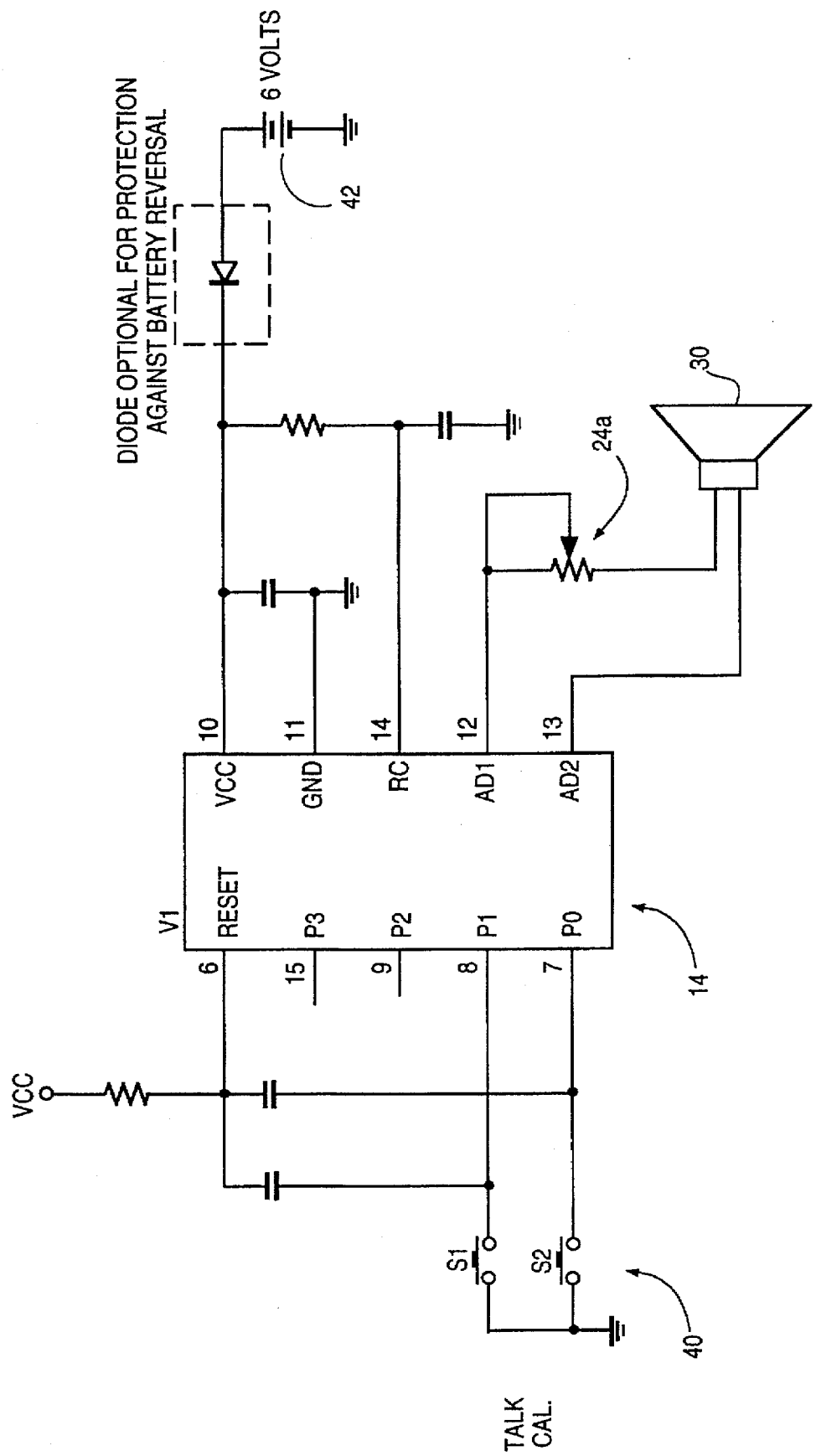
FIG. 3 is a schematic diagram of one implementation of the block diagram of FIG. 1.

FIG. 3 is a schematic diagram illustrating in more detail, various of the elements of the apparatus 10 where an audible output is desired. Elements in FIG. 3 which correspond to previously discussed elements of FIG. 1 have been identified with the same identification numeral.

The circuitry 14 is illustrated in FIG. 3 as being implemented by means of an ESS Technology, Inc. Speech Chip No. ES2108, which is commercially available. It will be understood that the particular form of integrated circuit or circuits used to implement the circuitry 14 is not a limitation of the present invention. The circuitry 14 also includes an output speaker and related controls.

FIGS. 4A through 4D illustrate various views of the housing 12 along with the components illustrated in FIG. 1. The housing 12 is formed with a cylindrical portion 50 which defines an interior region 52 wherein the electronic components 14 can be mounted.

The housing 12 includes one or more spacing, or positioning members, such as the members 56a and 56b. The members 56a and 56b are fixedly attached to the cylindrical portion 50 at proximal end regions 58a and 58b.

Distal end regions 60a and 60b are intended to be placed in contact with the side of the user's head adjacent to an ear with the ear positioned between the distal ends 60a and 60b. By way of example and not limitation, a spacing between the distal end regions 60a and 60b on the order of 2¼–2¾ inches, preferably about 2½ inches, has been found to be sufficient to accommodate most ears.

As is illustrated in FIGS. 4A and 4C, the positioning elements 56a and 56b are each formed with two spaced apart members, such as the members 56b-1 and 56b-2. The members 56b-1 and 56b-2 are fixedly attached to the cylindrical body portion 50 by proximal end regions 58b and are joined together by a distal end member 60b. An end surface 62b on the distal end member 60b is intended to be placed in contact with the side of the user's head.

The elements 56b-1, 56b-2, 60b and an end surface 50a bound an open region. A similar open region is associated with the spacing element 56a, and is bounded by elements 56a-1, 56a-2, 60a and surface 50a.

The spacing elements 56a and 56b as is illustrated in FIG. 4C, are spaced apart from one another and form an open cavity spacing element. These various openings provide a free sound field around the user's ear E.

By way of example, and not limitation, the distance between the end surface 60b or 62b and the end surface 50a preferably should fall in a range of 1½ inches to 2¼ inches, preferably about 2 inches. The length of the element 50 can be on the order of 1½ inches with its diameter on the order of 2 to 2½ inches to provide an overall size which is convenient to hold and manipulate.

The activation element 40, illustrated in FIGS. 4A through 4C, is located adjacent to a second end surface 50b of the housing 50. It will be understood that other locations are possible.

Control element 40 could be alternately located on a peripheral surface 50c, illustrated in FIG. 4C in phantom as element 40a. It will be understood that the exact location and number of the control elements 40 are not a limitation of the present invention.

FIG. 4D illustrates a bottom view of the housing 12. The end surface 50a can be perforated and/or covered with grillwork which is transparent to the audible words and phrases but which is intended to protect the transducer 30.

It will be understood that a closed cavity spacing element could be used without departing from the spirit and scope of the invention. Such a spacing element could have a generally cylindrical, continuous exterior wall and be affixed to a housing, such as the housing 50. The spacing element could have an end region, displaced from said housing transmissive of outputs from the transducer 30.

It will be understood that the spacing or positioning element not only can have various shapes but it need not be carried by the housing. For example, an output device could extend from an end of the housing. The positioning element could be carried by the output device.

It will be also understood that where a nonaudible output transducer 30 is used in lieu of a speaker for example, the dimensions of the positioning members 56a and 56b as well as their relative location with respect to the output transducer 30 would be adjusted to take into account the particular characteristics of that transducer. It will be understood that such adjustments come within the spirit and scope of the present invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A portable, self-contained hearing screening device to be placed adjacent to the outer ear of a user comprising:

a housing which defines an internal region and which has first and second spaced apart ends;

a control unit carried within the housing wherein a plurality of screening words is stored in the control unit;

a manually actuatable switch carried by the housing and coupled to the control unit;

an audio output transducer, carried within the housing, coupled to the control unit and oriented to output the screening words, one at a time in sequence, from one of the ends of the housing;

at least a first elongated displacement leg extending from the one end of the housing a predetermined distance and terminating at a positioning surface wherein the positioning surface is adapted to be placed adjacent to the ear of a user thereby displacing the output transducer from the user's ear substantially the distance determined by the displacement leg, wherein the displacement leg establishes an open region, between the output transducer and the positioning surface wherein the transducer outputs the screening words into the region and wherein the predetermined distance falls in a range of one and one-half to two and one-quarter inches.

2. A screening device as in claim 1 which includes first and second elongated, spaced apart, displacement legs wherein each of the legs extends from the one end of the housing, is coupled to the end of the housing at a respective junction and each of the legs terminates at a positioning surface and wherein the transducer is positioned adjacent to the one end of the housing between the junctions.

3. A screening device as in claim 2 which includes third and forth elongated displacement legs wherein the third and fourth legs are spaced apart from the first and second legs, wherein each of the legs is coupled to the one end of the housing at a respective junction, wherein the junctions are displaced from one another about a peripheral region of the one end and wherein the first and third legs and second and fourth legs define open regions therebetween.

4. A screening device as in claim 3 wherein the first and third legs are joined by an elongated positioning element displaced from the one end.

5. A screening device as in claim 4 wherein the second and fourth legs are joined by a second elongated positioning element displaced from the one end.

6. A hearing screening device positionable adjacent to a portion of a user's ear comprising:
   a housing having an output end which carries an audio output port and wherein that end defines a peripheral edge;
   a self-contained control unit, carried entirely within the housing, wherein the control unit is manually actuatable and adapted to emit a screening audio output from the port in response to the manual actuation;
   a plurality of elongated spaced apart spacing struts wherein each of the struts has first and second ends and a common length parameter, wherein each of the struts is attached at a respective first end to the housing at the peripheral edge with the respective second ends displaced from the output end a distance substantially corresponding to the common length parameter with each pair of struts defining an open peripheral region therebetween wherein the open region extends from the output end a distance substantially equal to the common length parameter.

7. A device as in claim 6 wherein each of the second ends is adapted to be placed adjacent to the user's ear thereby forming an audio output volume bounded only in part by the output end; the struts and the user's ear and wherein the output volume is not bounded by the struts in at least one peripheral region therebetween.

8. A device as in claim 6 wherein the plurality includes at least four struts and wherein the second ends of first and second of the struts have a first distance therebetween and the second ends of the first and third of the struts have a second, greater distance therebetween.

9. A device as in claim 6 wherein the control unit includes circuitry for storage of a list of vocabulary words to be emitted from the port.

10. A device as in claim 9 wherein the control circuit includes further circuitry for storage of at least one audible screening tone to be output from the port.

11. A hand held, self-contained screening device comprising:
    a closed housing which carries a manually operable switch and which has an output end;
    a circuit carried in the housing for generating an audio screening output at the output end in response to the manually operable switch; and
    at least one spacing leg having first and second ends, wherein the first end of the leg is coupled to the housing with the leg extending axially from the housing a predetermined length and wherein the second end is adapted to be placed adjacent to a user's ear thereby positioning the output end a distance from the ear substantially corresponding to the predetermined length thereby providing an open sound field between the ear and the output end bounded only in part by the ear, the output end and the spacing leg.

12. A device as in claim 11 wherein the predetermined length is in a range of one and one-half to two and one-quarter inches.

* * * * *